United States Patent [19]

Okada et al.

[11] Patent Number: 4,531,005
[45] Date of Patent: Jul. 23, 1985

[54] PYRAZOL-4-YL PHOSPHITES

[75] Inventors: Yoshiyuki Okada, Suita; Yoshihiro Inoue, Osaka; Koichi Iwanaga, Ibaraki, all of Japan

[73] Assignee: Takeda Chemical Industries, Ltd., Osaka, Japan

[21] Appl. No.: 582,135

[22] Filed: Feb. 23, 1984

Related U.S. Application Data

[63] Continuation of Ser. No. 345,760, Feb. 4, 1982, abandoned.

[30] Foreign Application Priority Data

Feb. 4, 1981 [JP] Japan .................................. 56-16104

[51] Int. Cl.³ ................................................. C07F 9/63
[52] U.S. Cl. ..................................................... 548/116
[58] Field of Search ......................................... 548/116

[56] References Cited

U.S. PATENT DOCUMENTS 4,315,008 2/1982 Maurer et al. .................... 548/116
4,474,775 10/1984 Okada et al. ................... 548/116 X

FOREIGN PATENT DOCUMENTS 3012193 10/1980 Fed. Rep. of Germany .
294598 2/1954 Switzerland ..................... 548/116

OTHER PUBLICATIONS

Houben–Weyl, Methoden Der Organischen Chemie, vol. XII/2, (1965), Georg Thieme Verlag, Stuttgart, pp. 73–78.
Kosolapoff et al., Organic Phosphorus Compounds, vol. 7, John Wiley & Sons, New York, (1978), pp. 537–539.

Primary Examiner—Richard L. Raymond
Attorney, Agent, or Firm—Burgess, Ryan & Wayne

[57] ABSTRACT

A 4-pyrazolyl phosphorous acid ester of the following formula,

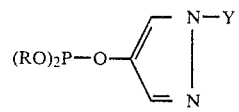

(R is a lower alkyl group; Y is a phenyl group which may optionally be substituted by a halogen, halogens, a lower alkyl group or a halogen and a lower alkyl group.) which is produced by reacting corresponding 4-hydroxylpyrazole compound with a trialkyl phosphite. The ester gives 4-pyrazolyl phosphorothioate by the reaction with an alkylsulfenyl halide.

3 Claims, No Drawings

PYRAZOL-4-YL PHOSPHITES

This is a continuation of application Ser. No. 345,760, filed Feb. 4, 1982 abandoned.

This invention relates to novel 4-pyrazolyl phosphites and a method for producing thereof as well as known 4-pyrazolyl phosphorothioates.

It is known that when a trialkyl phosphite is reacted with an alcohol containing a larger number of carbon atoms than the existing ester residues, a serial transesterification reaction takes place to yield a phosphorous acid ester having the ester residue group containing the larger number of carbon atoms (Methoden der Organisher Chemie XII/ Vol. 2, pp. 73 and 74, 1964).

The present inventors attempted at such transesterification reactions using, instead of alcohols, many aromatic hydroxy compounds such as phenols and heterocyclic hydroxy compounds such as 1-phenyl-3-hydroxypyrazoles and 1-phenyl-5-hydroxypyrazoles but none of these compounds gave rise to the desired reactions.

It was, however, found that 4-hydroxypyrazoles having a phenyl group in 1-position are able to give O,O-dialkyl-O-(1-substituted pyrazol-4-yl)phosphites in good yield and that these phosphorous acid esters are of use as intermediates for the production of 4-pyrazolyl phosphorothioates which are of value as agricultural insecticide and acaricide.

An object of this invention is to provide the O,O-dialkyl-O-(1-substituted pyrazol-4-yl)phosphites and a method for producing thereof.

Another object of this invention is to provide a method for producing the 4-pyrazolyl phosphorothioates.

This invention is therefore directed to the following aspects:

(1) A phosphorous acid ester derivative of the general formula

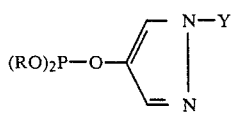

(R is a lower alkyl group; Y is a phenyl group which may optionally be substituted by a halogen, halogens, a lower alkyl group or a halogen and a lower alkyl group.), (2) A method for producing a phosphorous acid ester derivative of the general formula [I] which comprises reacting a 4-hydroxypyrazole derivative of the general formula

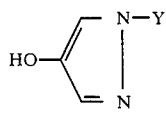

(Y is as defined above) with a trialkyl phosphite [III] and (3) A method for producing a compound of the general formula

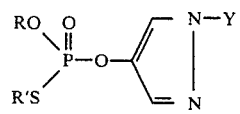

(R' is a lower alkyl group; R and Y are as above) which comprises reacting a phosphorous acid ester derivative of the general formula [I] with a lower alkylsulfenyl halide [IV].

Referring to the above general formula, Y is a phenyl which may optionally be substituted by one to three identical or different substituents, for example, a straight-chain or branched lower alkyl group such as methyl, ethyl, propyl, isopropyl, n-butyl, tert-butyl, etc., a lower alkoxy group such as methoxy, ethoxy, n-propoxy, isopropoxy, n-butoxy, sec-butoxy, etc., an alkylidenedioxy group such as methylenedioxy, isopropylidenedioxy, etc., a lower alkylthio group such as methylthio, ethylthio, n-propylthio, isopropylthio, n-butylthio, sec-butylthio, etc., a halogen such as fluorine, chlorine, bromine and iodine, nitro, trifluoromethyl and so forth. The substituents on the phenyl group are preferably methyl, fluorine, chlorine or/and bromine, for instance, and the number of the substituents is preferably 1 to 2.

Referring, further, to the general formulas, R and R' are the same or different and each is a straight-chain or branched lower alkyl group such as methyl, ethyl, propyl, isopropyl, n-butyl, isobutyl, sec-butyl, etc. The lower alkyl moiety of said lower alkylsulfenyl halide is as defined for R' and the halogen atom of the halide is, for example, chlorine or bromine. The alkyl moieties of said trialkyl phosphite ester are as defined for R.

The compound [I] of this invention can be produced by reacting a trialkyl phosphite [III] with a 4-hydroxypyrazole derivative [II]. The compound [III] can be used in a proportion, based on [II], of, generally, 1 to 20 molar equivalents and, preferably, 2 to 10 equivalents. Use of a larger excess of [III] is, however, not objectionable. In this reaction, [III] may generally be utilized as a solvent as well but the reaction may also be conducted in a solvent inert to the reaction, such as aromatic hydrocarbons (e.g. benzene, toluene, xylene) and ethers such as dioxane, diethylene glycol dimethyl ether, dimethylene glycol dimethyl ether, etc.

The reaction temperature may be optional within the range of 30° to 200° C. only if the reaction may proceed satisfactorily at the selected temperature, but the range of 50° to 160° C. is preferred in view of the fact that the reaction rate is generally too low at low temperatures and the thermal stability of the starting material trialkyl phosphite must be taken into consideration at higher temperatures. As an alcohol is produced in the course of this reaction, the progress of reaction can be rendered smooth by removing the alcohol from the reaction system. Thus, the reaction may be hastened by heating the reaction mixture to a temperature over the boiling point of the by-product alcohol at atmospheric or under reduced pressure so as to distill off the alcohol.

The reaction time may be established in relation with the reaction temperature. The reaction time is generally 0.5 to tens of hours and preferably in the range of 0.5 to 10 hours.

The progress of reaction may also be made smooth by using a catalyst. As examples of the catalyst may be mentioned such bases as tertiary amines (e.g. triethylamine, tripropylamine, tributylamine, N-methylmorpholine, N-methylpiperidine, N,N-dimethylaniline, pyridine, picoline, lutidine, etc.), salts of 1-substituted-4-hydroxypyrazole derivatives (e.g. 1-phenyl-4-hydroxypyrazole) with alkali metals (e.g. potassium, sodium, etc.), alkali metal alkoxides derived from alcohols (e.g. methanol, ethanol, propanol, butanol) and alkali metal phenolates derived from phenols, etc., and such acids as halides of metals of Groups II through VIII of Periodic Table of the Elements such as titanium, iron, cobalt, nickel, zinc, boron, aluminum, etc. [e.g. aluminum chloride, zinc chloride, nickel chloride, stannous chloride, stannic chloride, titanium trichloride, boron trifluoride, etc.].

The catalyst is generally used in a proportion of 0.1 to 10 mol percent based on compound [II]. The catalyst may be previously added to one of the starting materials or added to a reaction system containing the two starting materials. The reaction proceeds faster and at lower temperature than in the absence of a catalyst.

The phosphorous acid ester derivative [I] can be reacted with a lower alkylsulfenyl halide [IV] to produce a compound of formula [V]. This reaction is preferably conducted in an inert solvent, examples of which are aliphatic hydrocarbons such as n-pentane, n-hexane, ligroine, etc., aromatic hydrocarbons such as benzene, toluene, xylene, etc., halogenated hydrocarbons such as methylene chloride, chloroform, carbon tetrachloride, ethylene chloride, chlorobenzene, etc. and ethers such as ethyl ether, isopropyl ether, dioxane, tetrahydrofuran, etc.

The above-mentioned solvents may be used either alone or as a mixture of two or more of them, for example in a ratio of 1:1 to 1:10.

The alkylsulfenyl halide [IV], which is one of reactants, can be produced by, for example, the method described in Organic Functional Group Preparations Vol. 3, 150–163, 1972, Academic Press, New York and London.

Generally, in admixing the both starting compounds for the contemplated reaction, the phosphorous acid ester derivative [I] is added to the lower alkylsulfenyl halide [IV] or the latter to the former, care being used to maintain the mixture at a temperature which does not decompose the alkylsulfenyl halide [IV], for example a comparatively low temperature of −20° C. to +50° C. As the two reactants are admixed, an addition compound is first produced and precipitates out in many cases. As the system is subsequently heated to 20°–100° C. for 0.5 to 10 hours, the alkyl halide is liberated to yield the desired compound. This compound [I] or [V] can be isolated and purified by per se conventional procedures such as concentration at atmospheric or under reduced pressure, distillation, fractional distillation, solvent extraction, pH adjustment, redistribution, crystallization, recrystallization and chromatography.

The compound [V] is of value, for example, as an agricultural insecticide/acaricide as described in OLS 2854389 and OLS 3012193, for instance.

The following examples are intended to illustrate this invention in further detail and should by no means be construed as limiting the scope of the invention.

In the examples, a product which belongs to the formula [I] was analyzed by a gas chromatography, while a product belonging to the formula [V] was analyzed by a high pressure liquid chromatography. The both chromatographic analysis were carried out under the following conditions.

Gas Chromatography

Packing: 1.5% silicone OV-17 (made by Shimadzu Corporation, Japan)
Column: 1.5 m×3φ
Column temp.: 220° C.
Injection temp.: 250° C.
Carrier gas: N₂ 60 ml/min.
Detector: FID
Instrument: Shimadzu GC-7AG High Pressure Liquid Chromatography Column: ODS(C-18) 4φ×25 cm
Temp.: 40° C.
Mobile phase: acetone/water (65/35 Vol./Vol.)
Flow rate: 1.6 ml/min.
Excitation wavelength: 254 nm
Instrument: Shimadzu LC-3A

EXAMPLE 1

O-[1-(4-Chlorophenyl)pyrazol-4-yl]-O,O-diethyl phosphite 99.7 g (0.6 mol) of triethyl phosphite and 19.4 g (0.1 mol) of 1-(4-chlorophenyl)-4-hydroxypyrazole are weighed into a three-necked flask of 200 ml capacity. The flask is fitted with a Vigreaux fractionating column and a cooling condenser. Under reduced pressure, the reaction mixture is heated on an oil bath at 160° C. With progress of the reaction, ethanol is distilled off. The reaction is allowed to continue for 7 hours, at the end of which time the excess triethyl phosphite is removed under reduced pressure to give 31.7 g of an oily residue. Gas chromatographic analysis of this product shows that the content of the above-identified compound is 92.6 weight %.

Table 1 is a partial listing of compounds [I] which can be produced in the same manner as Example 1.

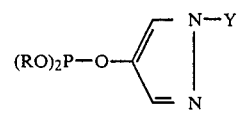

TABLE 1

| Example No. | R | Y | Boiling point (°C./mmHg) |
|---|---|---|---|
| 1 | C₂H₅ | ⟨phenyl⟩—Cl | 145/0.1 |
| 2 | C₂H₅ | ⟨phenyl⟩ | 152–154/0.2 |
| 3 | C₂H₅ | ⟨phenyl with Cl (ortho)⟩ | 161–162/0.15 |
| 4 | C₂H₅ | ⟨phenyl⟩—CH₃ | 142–143/0.1 |

TABLE 1-continued

| Example No. | R | Y | Boiling point (°C./mmHg) |
|---|---|---|---|
| 5 | $C_2H_5$ | $CH_3$, 4-Cl-phenyl | 162–164/0.15 |
| 6 | $C_2H_5$ | F, 4-Cl-phenyl | 153–155/0.3 |
| 7 | $C_2H_5$ | Cl, 4-Cl-phenyl | 152/0.2 |
| 8 | $n$-$C_3H_7$ | 4-Cl-phenyl | 175/0.15 |
| 9 | $i$-$C_3H_7$ | 4-Cl-phenyl | 155–156/0.3 |
| 10 | $n$-$C_4H_9$ | 4-Cl-phenyl | 200–203/0.2 |

EXAMPLE 11

O-[1-(4-Chlorophenyl)pyrazol-4-yl]-O,O-diethyl phosphite 99.7 g (0.6 mol) of triethyl phosphite, 19.4 g (0.1 mol) of 1-(4-chlorophenyl)-4-hydroxypyrazole and, as a catalyst, 1.0 g (0.005 mol) of sufficiently dried 1-(4-chlorophenyl)-4-hydroxypyrazole sodium salt are weighed into a three-necked flask of 200 ml capacity. The flask is fitted with a Vigreaux fractionating column and a cooling condenser. Under mild evacuation, the reaction mixture is heated to 100° C. on an oil bath. With progress of the reaction, ethanol is distilled off. The reaction is allowed to proceed for 2 hours, at the end of which time insolubles are filtered off and the excess triethyl phosphite is distilled off under reduced pressure to give 30.2 g of an oily residue. Gas chromatographic analysis of this product shows that the content of the above-identified compound is 95.2 weight %.

Table 2 shows some production examples, including the above Example 11, of O-[1-(4-chlorophenyl)-pyrazol-4-yl]-O,O-diethyl phosphite as produced with different catalysts.

TABLE 2

| Example No. | Catalyst (5 mol %) | Reaction temperature (°C.) | Reaction time (hrs) | Triethyl Phosphite (mols) | Yield (g) | Content of (I) (%) | Yield (%) |
|---|---|---|---|---|---|---|---|
| 11 | A | 100 | 2 | 0.6 | 30.2 | 95.5 | 91.6 |
| 12 | A | 100 | 2 | 0.3 | 29.1 | 96.3 | 89.0 |
| 13 | B | 100 | 4 | 0.6 | 30.4 | 87.2 | 84.2 |
| 14 | B | 100 | 4 | 0.3 | 30.9 | 86.2 | 84.6 |
| 15 | C | 100 | 4 | 0.3 | 32.1 | 89.7 | 91.5 |
| 16 | D | 100 | 4 | 0.3 | 31.4 | 84.2 | 84.0 |
| 17 | E | 100 | 4 | 0.3 | 30.4 | 78.1 | 75.4 |

*: A denotes 1-(4-chlorophenyl)-4-hydroxypyrazole sodium salt;
B, $ZnCl_2$;
C, $NiCl_2$;
D, $SnCl_2$; and
E, $BF_3.O(C_2H_5)_2$.

EXAMPLE 18

O-[1-(4-Chlorophenyl)pyrazol-4-yl]-O-ethyl-S-n-propyl phosphorothioate

In 40 ml of toluene is dissolved 1.5 g (0.01 mol) of n-propyl disulfide and the solution is cooled to −5° C. Thereafter, 1.4 g (0.01 mol) of sulfuryl chloride is added portionwise. The mixture is stirred at that temperature for 1.5 hours, after which 6.2 g (0.02 mol) of O-[1-(4-chlorophenyl)pyrazol-4-yl]-O,O-diethyl phosphite is added at −5~0° C. Thereafter, the reaction mixture is stirred at room temperature for an hour, during which white crystals separate out gradually. The reaction mixture is then heated at 60°–70° C. for an hour, whereby the crystals are dissolved with evolution of gases to yield a homogeneous solution. After this reaction, the toluene layer is washed with a 2% aqueous solution of sodium hydroxide and, then, thoroughly with water. The solution is dried over anhydrous sodium sulfate and the toluene is distilled off under reduced pressure to give 6.5 g of a yellow oil. This residue is purified by silica gel column chromatography (eluent:chloroform) to give 5.6 g of the above-identified compound. $n_D^{24}$ 1.5604. The IR and NMR spectra of this product are identical with those of the standard sample.

EXAMPLE 19

O-[1-(4-Chlorophenyl)pyrazol-4-yl]-O-ethyl-S-n-propyl phosphorothioate

In 150 ml of toluene is dissolved 7.1 g of n-propyl disulfide, followed by cooling to −5° C. Then, 6.3 g of sulfuryl chloride is added portionwise at the same temperature. The mixture is stirred for 1.5 hours, at the end of which time 31.7 g of a crude preparation of O-[1-(4-chlorophenyl)pyrazol-4-yl]-O,O-diethyl phosphite as obtained in Example 1 is added at −5~0° C. Thereafter, the mixture is stirred at room temperature for an hour and, then, heated at 70° C. for 3 hours. After this reaction is complete, the toluene layer is washed with a 2% aqueous solution of sodium hydroxide and, then, thoroughly with water. The solution is dried over anhydrous sodium sulfate and the toluene distilled off under reduced pressure to give 32.2 g of a yellow oil. High pressure liquid chromatographic analysis of this product shows that the content of the above-identified compound is 93.3 weight %.

EXAMPLE 20

S-sec-Butyl-O-[1-4-chlorophenyl)pyrazol-4-yl]-O-n-propyl phosphorothioate

In 50 ml of toluene is dissolved 0.9 g (0.005 mol) of sec-butyl disulfide, followed by cooling to −5° C. Then, 0.7 g (0.005 mol) of sulfuryl chloride is added portionwise. The mixture is stirred at that temperature for 1.5 hours, after which 3.4 g (0.01 mol) of O-[1-(4-chlorophenyl)pyrazol-4-yl]-O,O-di-n-propyl phosphite is added at −5∼0° C. The mixture is stirred at room temperature for an hour and, then, heated at 70° C. for 5 hours. Thereafter, the reaction mixture is worked up in the same manner as Example 18 to give 2.7 g of the above-identified compound as a pale yellow oil. $n_D^{24}$ 1.5474.

EXAMPLE 21

S-sec-Butyl-O-ethyl-O-(1-phenylpyrazol-4-yl)phosphorothioate

In 40 ml of toluene is dissolved 0.9 g (0.005 mol) of sec-butyl disulfide, followed by cooling to −5° C. Then, 0.7 g (0.005 mol) of sulfuryl chloride is added portionwise and the mixture is stirred at the above temperature for 1.5 hours, at the end of which 2.8 g (0.01 mol) of O,O-diethyl-O-(1-phenylpyrazol-4-yl)phosphite is added at −5∼0° C. The mixture is then stirred at room temperature for an hour, during which white crystals separate out gradually. The mixture is then heated at 80° C. for 2 hours, whereby the crystals dissolve to yield a homogeneous solution.

Thereafter, the solution is worked up in the same manner as Example 18 to give 2.2 g of the above-identified compound as a pale yellow oil. $n_D^{20}$ 1.5457.

Each product obtained in Examples 11 to 17 was converted to O-[1-(4-chlorophenyl)pyrazol-4-yl]-O-ethyl-S-n-propyl phosphorothioate in the same manner as described in Example 19 and the experiments were allotted Example numbers 22 to 28 corresponding to Examples 11 to 17, respectively.

The yields of the phosphorothioate are shown in Table 3 as well as those of products in Examples 11 to 17.

TABLE 3

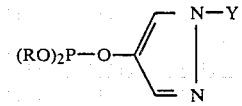

| Example No. | Amount of product (g) | Content (%) | Yield (%) | Example No. | Amount of product (g) | Content (%) | Yield* (%) |
|---|---|---|---|---|---|---|---|
| 11 | 30.2 | 95.5 | 1.6 | 22 | 33.2 | 91.1 | 81.3 |
| 12 | 29.1 | 96.3 | 89.0 | 23 | 33.1 | 83.8 | 76.9 |
| 13 | 30.4 | 87.2 | 84.2 | 24 | 31.8 | 95.7 | 84.4 |
| 14 | 30.9 | 86.2 | 84.6 | 25 | 32.2 | 95.4 | 85.1 |
| 15 | 32.1 | 89.7 | 91.5 | 26 | 31.4 | 93.0 | 80.9 |
| 16 | 31.4 | 84.2 | 84.0 | 27 | 32.4 | 91.6 | 82.3 |
| 17 | 30.4 | 78.1 | 75.4 | 28 | 24.4 | 91.6 | 61.9 |

*This yield is calculated basing on 1-(4-chlorophenyl)-4-hydroxypyrazole.

We claim:

1. A phosphorous acid ester derivative of the general formula $$(RO)_2P-O-\underset{N}{\overset{N-Y}{\diagdown}}$$

wherein R is ethyl; Y is a phenyl group which is substituted by one or more halogens, a trifluoromethyl, a lower alkyl group or a halogen and a lower alkyl group.

2. A compound according to claim 1, wherein Y is a phenyl group substituted by one or more chlorines, a chlorine and a fluorine, a methyl group or a chlorine and a methyl group.

3. O-[1-(4-chlorophenyl)pyrazol-4-yl]-O,O-diethyl phosphite.

* * * * *